(12) United States Patent
Kleen et al.

(10) Patent No.: US 7,979,106 B2
(45) Date of Patent: Jul. 12, 2011

(54) SYSTEM AND METHOD FOR POSITIONING MEDICAL DEVICES

(75) Inventors: Martin Kleen, Furth (DE); Rainer Kuth, Herzogenaurach (DE)

(73) Assignee: Siemens Aktiengesellschaft, Munich (DE)

( * ) Notice: Subject to any disclaimer, the term of this patent is extended or adjusted under 35 U.S.C. 154(b) by 1586 days.

(21) Appl. No.: 11/328,474

(22) Filed: Jan. 9, 2006

(65) Prior Publication Data

US 2006/0169288 A1 Aug. 3, 2006

(30) Foreign Application Priority Data

Jan. 10, 2005 (DE) .......................... 10 2005 001 133

(51) Int. Cl.
*A61B 5/05* (2006.01)

(52) U.S. Cl. ..... 600/407; 600/473; 600/476; 250/358.1; 345/158

(58) Field of Classification Search .................. 600/407, 600/473, 476; 250/358.1; 345/158
See application file for complete search history.

(56) References Cited

U.S. PATENT DOCUMENTS

| | | | |
|---|---|---|---|
| 4,853,771 A * | 8/1989 | Witriol et al. ................... 348/94 |
| 5,086,401 A | 2/1992 | Glassman et al. | |
| 5,097,495 A | 3/1992 | Gray et al. | |
| 5,166,588 A | 11/1992 | Goldhorn | |
| 5,570,770 A | 11/1996 | Baaten et al. | |
| 5,901,236 A * | 5/1999 | Mizui ........................... 382/104 |
| 6,272,368 B1 * | 8/2001 | Alexandrescu ............... 600/407 |
| 6,973,202 B2 * | 12/2005 | Mostafavi ..................... 382/103 |
| 7,657,301 B2 * | 2/2010 | Mate et al. .................... 600/424 |
| 2004/0261179 A1 | 12/2004 | Blumenkranz | |

FOREIGN PATENT DOCUMENTS

| | | |
|---|---|---|
| DE | 692 05 313 T2 | 9/1992 |
| DE | 693 27 436 T2 | 3/1994 |
| EP | 0 087 198 B1 | 8/1983 |
| EP | 0 445 330 A1 | 9/1991 |
| EP | 0 456 103 A2 | 11/1991 |

* cited by examiner

*Primary Examiner* — Brian Casler
*Assistant Examiner* — James Kish

(57) ABSTRACT

In order, despite a plurality of terminals, to enable their freedom of movement on the one hand and an unimpeded treatment process on the other hand to be guaranteed, there is provision in accordance with the invention, for recording the devices in their envisaged spatial distribution, especially by at least one camera, to check this distribution as regards a sufficient freedom of movement of the devices, especially by a processing or control unit, and to feed back a corrected distribution, especially by at least one video projector.

16 Claims, 4 Drawing Sheets

SYSTEM AND METHOD FOR POSITIONING MEDICAL DEVICES

CROSS REFERENCE TO RELATED APPLICATIONS

This application claims priority to the German Application No. 10 2005 001 133.0, filed Jan. 10, 2005 which is incorporated by reference herein in its entirety.

FIELD OF INVENTION

The invention relates to a system or a method for positioning devices which can be assigned to a patient to be treated within said patient's environment.

BACKGROUND OF INVENTION

A plurality of devices are frequently required for the treatment of a patient, said devices being assigned to the patient is his or her environment. For a surgical intervention under anesthesia a table with surgical instruments, measuring devices for monitoring the anesthetic and also a ventilator are arranged around an operating table with the patient. To perform the operation it may be necessary to provide further instruments, such as an operation microscope for example. In emergency situations it can also be necessary to rapidly deploy further devices such as a C-arm x-ray system or a defibrillator.

SUMMARY OF INVENTION

Since cables of tubes lead to the patient from a number of devices such as from the ECG monitor or the ventilation device for example and a few of the devices, such as the operation microscope and the C-arm system, have parts which can be swiveled, there is the danger of these devices and the persons performing the treatment interfering with each other's freedom of movement or of collisions occurring between them, which renders the treatment more difficult.

An object of the invention is, despite a plurality of devices set up in the vicinity of the patient to be treated or only to be put into position during the treatment of the patient, to provided a simple way of enabling an unimpeded treatment process to be guaranteed.

This object is achieved by the claims.

Starting from a pre-positioning in respect of freedom of movement and avoidance of collisions as well as unimpeded access to the devices needed for treatment which may not be optimum or may even be hazardous on the floor surface of the treatment room, the inventive recording and checking of the pre-positioning and also feedback of the checking before or during the treatment for the persons performing the treatment enables at least one corresponding warning to be issued rapidly and safely when freedom of movement and freedom from collisions is not guaranteed or furthermore an appropriately optimized positioning to be displayed.

In an advantageous manner not only are the pre-positioned devices taken into consideration in the checking but also at least one additional device necessary in an emergency situation by a blocked area reserved in the spatial distribution for this device; By including this blocked area to be kept free initially, on which no other devices are to be positioned, the additional device can be introduced immediately into the existing spatial distribution in the emergency situation for treatment of the patient.

In a further embodiment of the invention the inclusion of an area of movement for at least one person performing the treatment is provided in the spatial distribution; The additional consideration of persons provided for treating the patient as well as the devices guarantees their freedom of movement despite a plurality of devices to be distributed on the floor space of the treatment room.

An especially secure and precise recording of the devices in their spatial distribution is produced by a camera as a first system component, especially arranged above the devices or the floor space. An electronic processing or control unit provided for checking the spatial distribution which has information about data relating to degree of freedom of movement and/or 3D extent of the relevant devices and/or type and scope of the treatment of the patient, represents a technically particularly simple embodiment of the second system component.

For feedback an acoustic signal generator requiring little effort to implement can simply be provided as a third system component. Such a signal generator can also advantageously provide spoken instructions for correcting the spatial distribution if the pre-positioning is not optimum. In accordance with a further embodiment of the third system component in the form of a optical signal generator, especially in the form of a video projector or of a laser beamer. the feedback can be further enhanced by projecting the optimum positions of the devices directly onto the relevant positions in the treatment room.

BRIEF DESCRIPTION OF THE DRAWINGS

The invention, as well as further advantageous embodiments of the invention in accordance with features of the subclaims, are explained in greater detail below with reference to schematic diagrams of exemplary embodiments in the drawing, without this restricting the invention to this exemplary embodiment in any way; The Figures show:

DETAILED DESCRIPTION OF INVENTION

Figure 1:
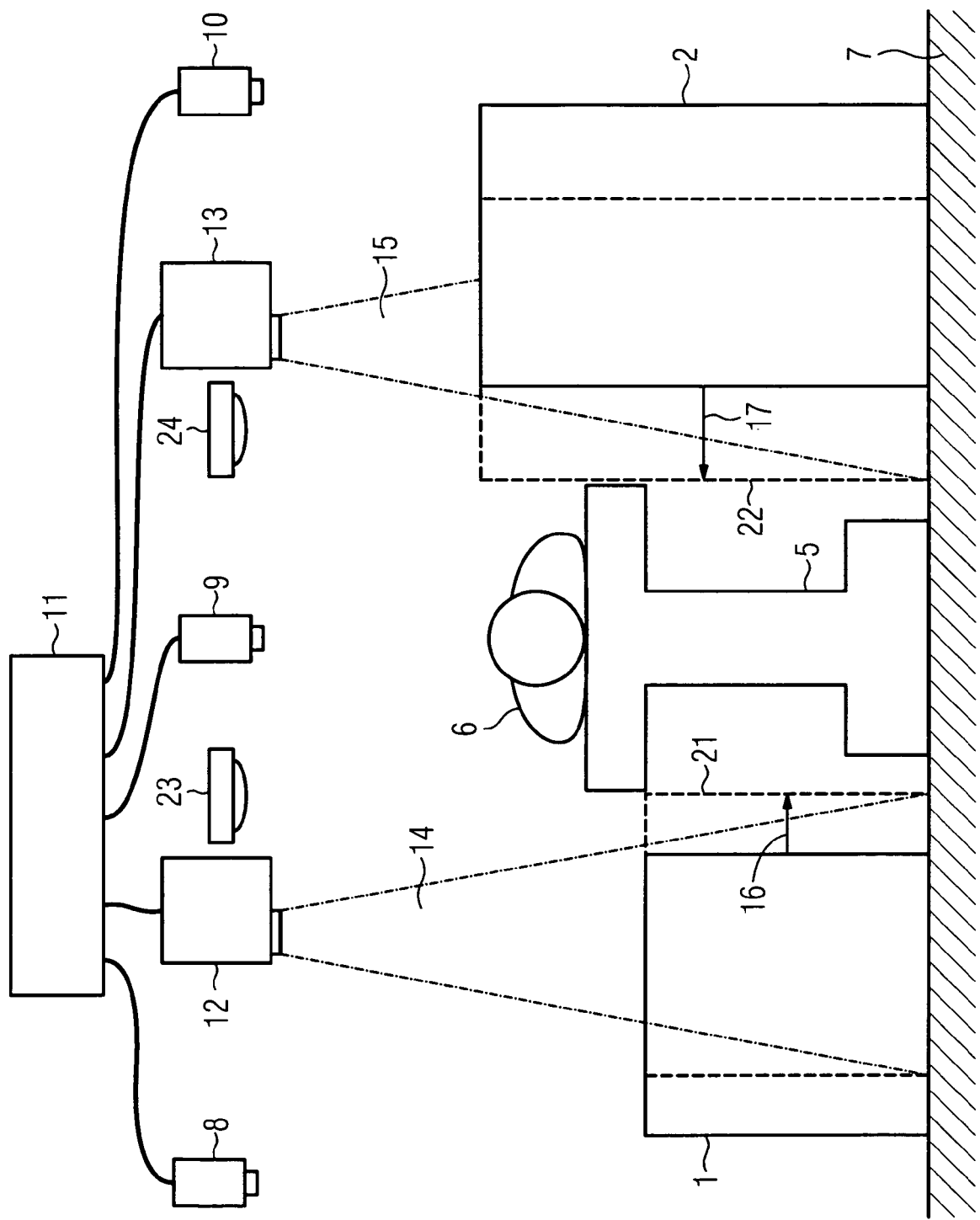
FIG. 1 a side view of a spatial distribution of devices around a patient table on the floor space of a treatment room, with cameras being provided for recording the devices and video projectors being provided for feedback.

FIG. 1 shows a side view of a spatial distribution of pre-positioned devices 1, 2 around a patient table 5 with a patient 6 on a floor space 7 of a treatment room. Above the devices 1, 2 or above the floor space 7 are cameras 8-10 arranged as first system components, which record the devices 1, 2 in their initially intended spatial distribution.

An electronic processing or control unit 11 linked to the cameras 8-10 is provided as a second system component, which checks the intended spatial distribution, taking into account the degree of freedom of movement and/or the 3D extension of the devices 1, 2 and where necessary the type and scope of the processing, especially through a movement simulation. In the movement simulation a plurality of movement sequences of devices 1, 2, but also where necessary of a person involved in the treatment are simulated, to enable the danger of possible collisions to be checked even before treatment.

The data as regards degree of freedom of movement and/or 3D extension is retrieved in a simple manner from an internal or external database. The database can for example be specified with the system or processed afterwards, especially by a learning mode. The data regarding the type and scope of treatment, from which for example the number of persons involved in the treatment and their function is also produced, can be retrieved especially from a hospital information system which may already be available but is not shown separately in this diagram.

Video projectors 12, 13 activated by the processing or control unit 11 are provided as third system components for feeding back the checks in the form of a projected position display of the corrected spatial distribution of the devices 1, 2 in the form of projected video light signals 14, 15. The projected video light signals 14, 15 show that the devices 1 and 2 are to be moved for an optimized spatial distribution in direction 16 or 17 towards the patient table 5 to the positions 21 or 22 shown by dashed lines.

In accordance with an advantageous embodiment of the invention the floor area 7 has a coating which reflects a light, especially infrared light. This makes possible, especially on illumination of the floor space 7 with two infrared lights 23, 24, a better recording of a part of the floor space free from devices 1, 2, e.g. usable as an area of movement by persons performing the treatment.

Figure 2:
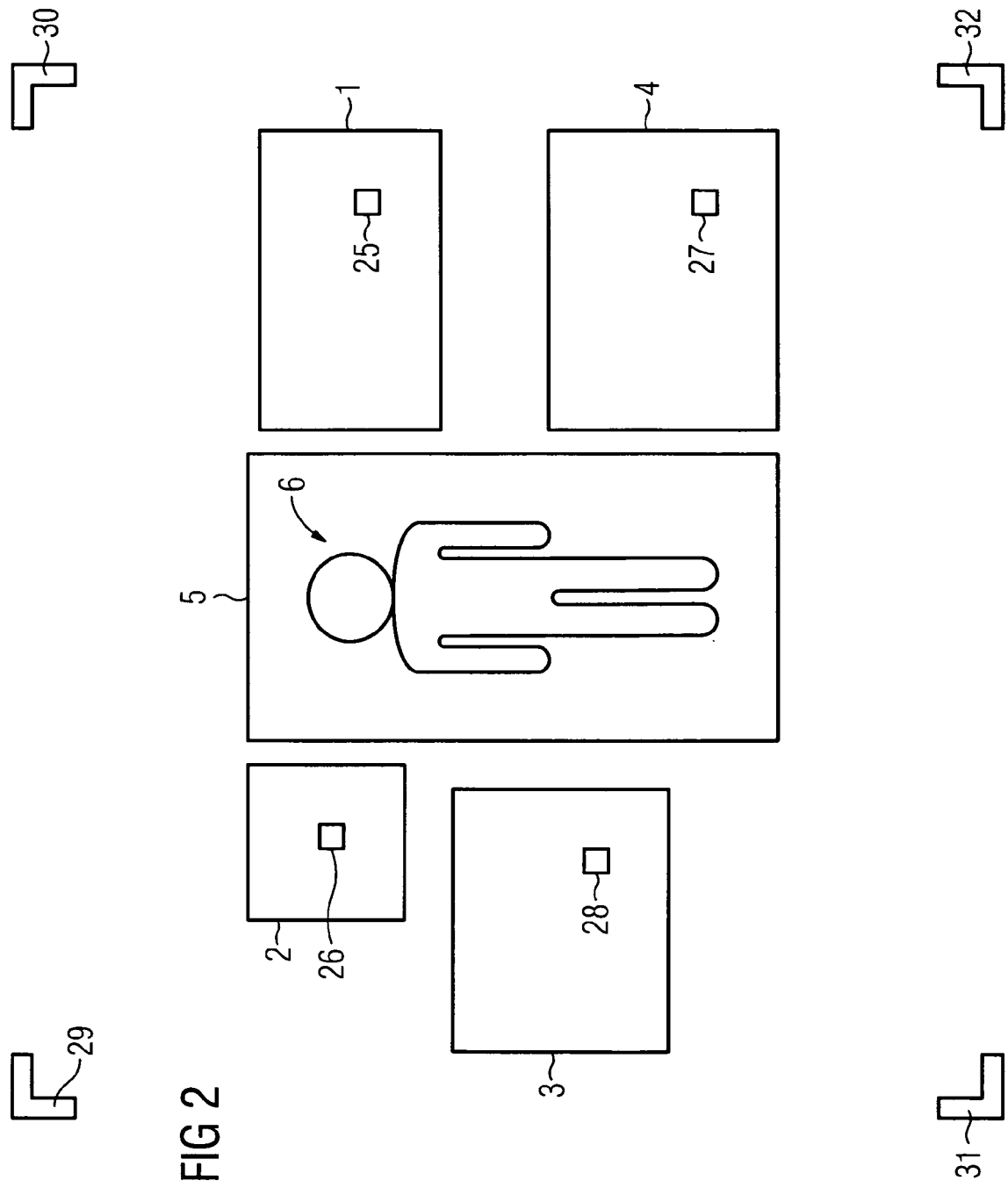
FIG. 2 viewed from above devices in an intended initial spatial arrangement around the patient table, with the devices being assigned markers.
Figure 3:
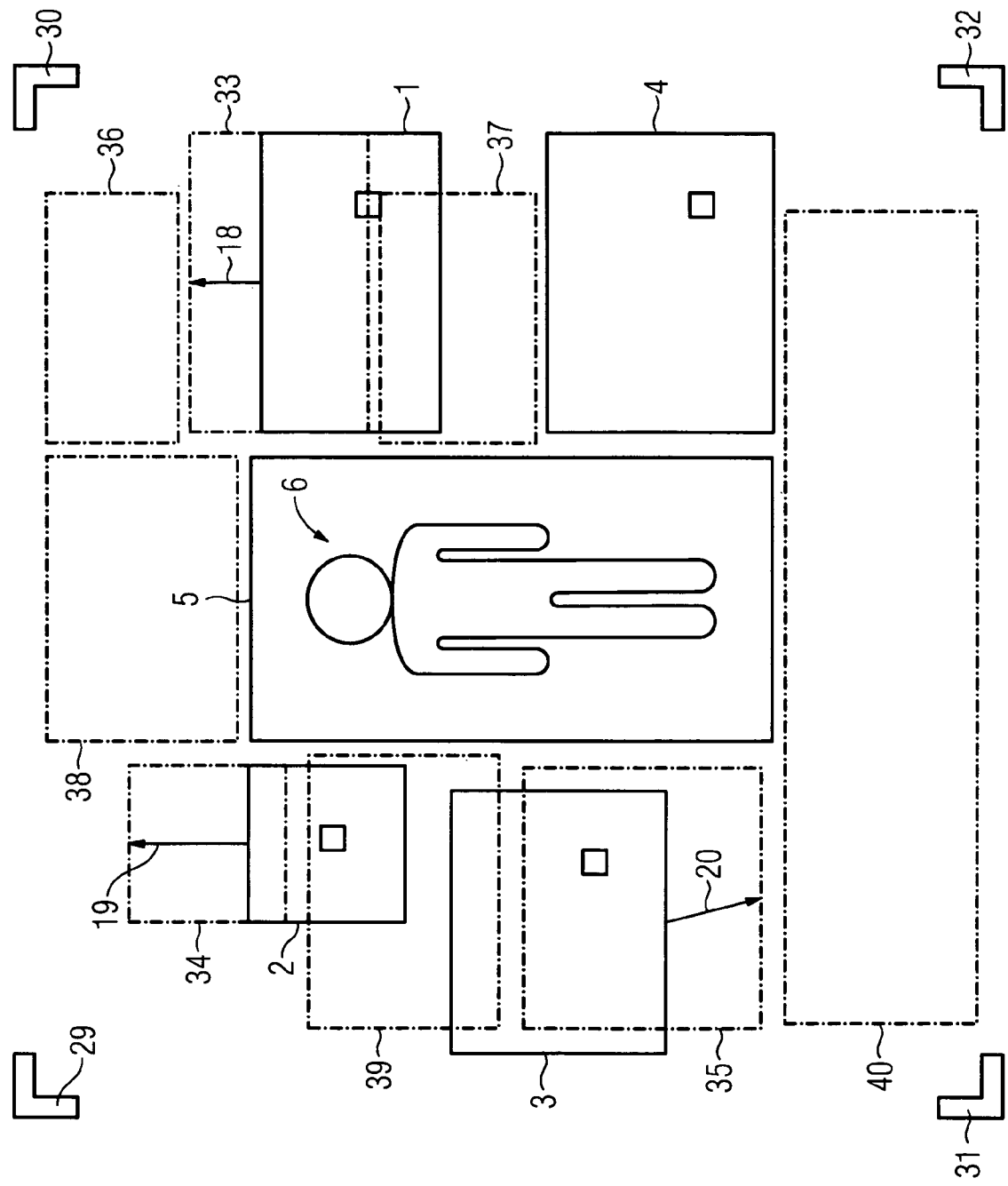
FIG. 3 the arrangement in accordance with FIG. 4 with a video projection of a corrected spatial distribution being provided for feeding back a check of the initial spatial distribution.
Figure 4:
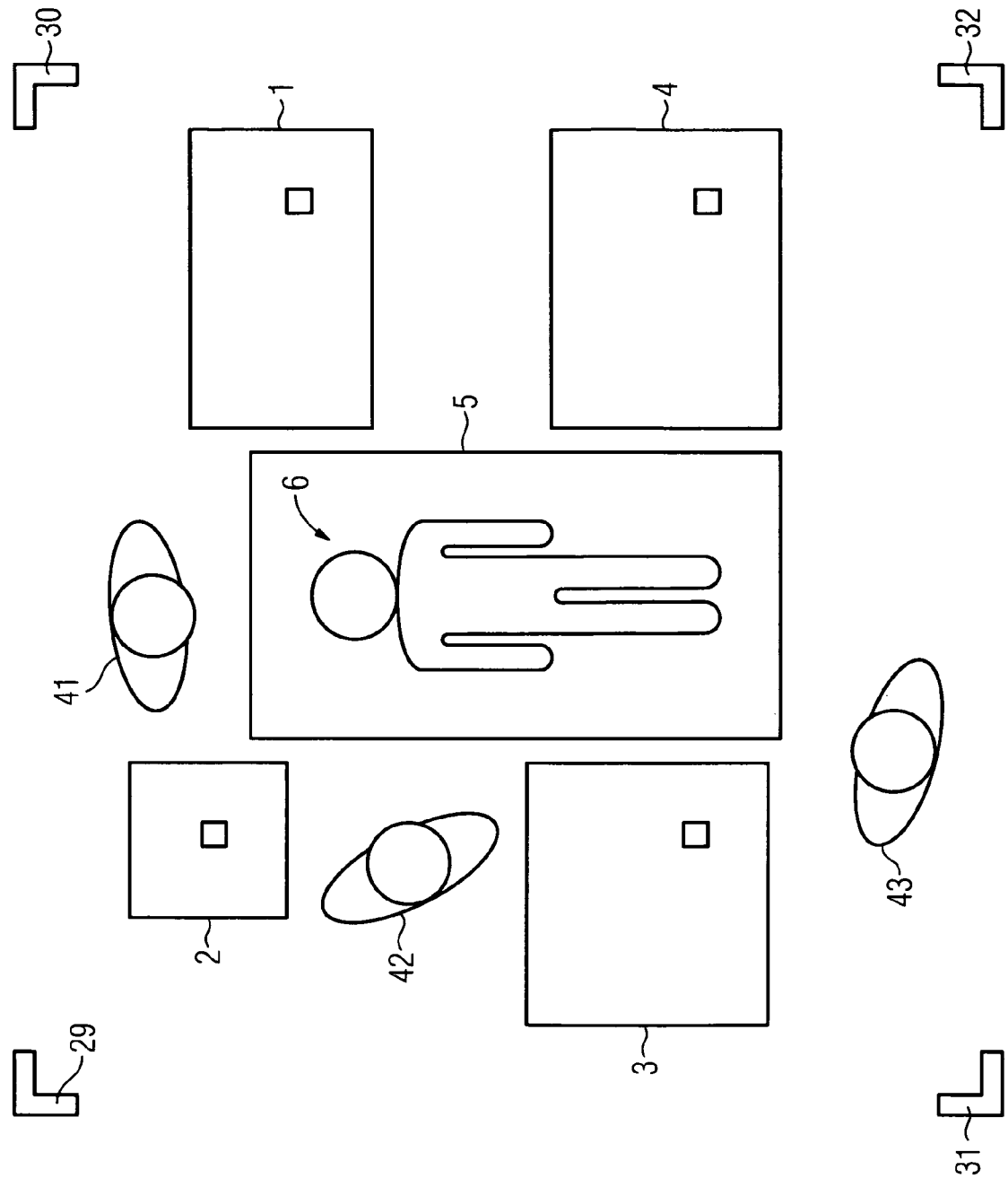
FIG. 4 the arrangement in accordance with FIG. 4 where the devices are positioned in their corrected spatial distribution and three persons performing the treatment are standing in the movement areas provided for them.

FIGS. 2-4 show three consecutive phases of a chronological positioning sequence.

FIG. 2 shows a view from above of devices 1-4 on the floor space in an intended spatial distribution before treatment—which differs from FIG. 1 in the changed positions of the devices 1, 2 already shown in that figure—around the patient table 5. For especially reliable recording of the devices 1-4 each device 1-4 is assigned a marker 25-28; These markers 25-28 are advantageous for recording the devices 1-4, since they make it easier to identify the devices 1-4 and to determine their positions.

Markers which fluoresce or emit light themselves, especially infrared light, allow an especially simple and safe recording even under difficult ambient lighting conditions. In an especially advantageous manner markers which emit the light in pulses are provided, with the relevant status information, especially for device identification, able to be reproduced by the corresponding pulse codings.

The recordability of the devices 1-4 in a technically simple manner is improved by markers 25-28 which reflect when illuminated by light, especially infrared light. To enable these markers 25-28 and/or the floor space 7 reflecting the light to be recorded especially reliably, in accordance with a further embodiment, at least one lamp illuminating the markers 25-28 and/or the floor space 7, especially at least one infrared lamp 23, 24 shown in FIG. 1 is provided.

For the corrections of the spatial positions a recording of the dimensions of the treatment room is useful; This is made possible in a simple manner by corresponding markers 29-32 arranged on the floor space 7 or by corresponding markers arranged on a wall not shown in the diagram. The room dimensions can be taken into account in the checking by the processing or control unit 11, especially in the movement simulation, so that the available floor area 7 and the restrictions to the freedom of movement by the at least one wall surface can be included in the checking.

FIG. 3 depicts devices 1-4 with a solid outline in the spatial distribution in accordance with FIG. 2 and with a dashed outline the spatial distribution in accordance with the feedback in the form of video projections 33-35 after a check on the distribution. In this case the corrected positions of the devices 1, 2, 3 are depicted by the video projections 33 or 34 or 35; In this case the devices 1, 2, 3 are to be moved in the directions indicated by the movement arrows 18 or 19 or 20 in each case for an optimum spatial distribution as regards freedom of movement and avoidance of collisions. Since the device 4—in accordance with the present example—is already at an optimum position, the video projection of the corresponding position indication covers the same area as the original position of device 4.

As further feedback from the checking, two video projections 36, 37 indicate two blocked areas on which in an emergency situation devices which are required rapidly, such as a defibrillator or a C-arm x-ray system, can be placed. In addition movement areas for the persons performing the treatment are shown by the further video projections 38-40.

To make it easier to distinguish the positions of the corrected spatial distribution indicated by the video projections 33-40 there is provision is accordance with an advantageous embodiment for showing the relevant position by specific colors and/or a specific plain text display. For example all blocked areas could be shown by a red video projection 36, 37, all movement areas by a blue video projection 38-40 and the corrected device positions by video projections 33-35 in a different color in each case with additional plain text displays of the relevant device names.

FIG. 4 shows the devices 1-4 from FIG. 3 after they have been moved to the device positions in accordance with the corrected spatial distribution shown by video projections 33-40 in FIG. 3 as well as three persons 41-43 performing the treatment on the movement areas provided for them and shown in FIG. 3 by video projections 38-40.

Many devices which can be transported with the patient 6, e.g. from a waiting room into the treatment room are supplied with power by means of rechargeable batteries during transport, with these devices able to be connected to a power supply network available in the treatment room for a longer stay in the treatment room, e.g. for a surgical intervention under anesthetic, to guarantee continuous operation of the devices and to recharge the batteries if necessary. In this context the fact that the devices have not been connected to the power supply can be shown by the corresponding pulse coding of the light emitted by the markers and a corresponding warning signal can be triggered by the processing or control unit 11.

Storage containers or consumables containers with further markers can be provided as further devices. If the relevant consumables are running low, this can be indicated by markers emitting a pulsed light in the pulse-coded status information or by a light-reflecting marker which becomes visible when the container is completely empty.

The invention can basically be summarized as follows: The invention relates to a system or a method for positioning devices 1-4 which can be assigned to a patient to be treated 6 in said patient's environment, with the intended spatial distribution of the devices 1-4 being recorded, especially by at least one camera 8-10, this distribution being checked as regards sufficient freedom of movement of the devices 1-4, especially by a processing or control unit 11 and a corrected distribution, especially by at least one video projector 12, 13 being fed back, so that, despite the plurality of devices 1-4, it is possible to guarantee an unimpeded treatment process and to avoid collisions.

The invention claimed is:

1. A system for indicating a recommended spatial distribution of devices configured to be assigned to a patient under medical treatment in a treatment room, the system comprising:
   a first system component means for registering the devices in a pre-arranged spatial distribution relative to the patient on a patient table, wherein the patient table is placed on a floor area of the treatment room;
   a second system component means for checking the spatial distribution relative to a desirable freedom of movement of the devices, wherein the second system component has data related to a spatial expansion of at least one of the devices and a scope of the treatment; and
   a third system component means for generating a feedback based on the checked spatial distribution and indicating the recommended spatial distribution of the devices based on the feedback,
   wherein the third system component is a video projector that indicates the recommended spatial distribution of the devices.

2. The system in accordance with claim 1, wherein the first system component is at least one camera.

3. The system in accordance with claim 1, further comprising a marker assigned to at least one of the devices or to the floor area or to a wall area, the marker provided as a registering aid.

4. The system in accordance with claim 3, wherein the marker is configured to indicate information about a type and an arrangement position of the respective device.

5. The system in accordance with claim 3, wherein the marker is configured to emit or fluoresce light.

6. The system in accordance with claim 5, wherein the marker is configured to emit light pulses, the light pulses representing pulse-coded status information related to the respective device.

7. The system in accordance with claim 3, wherein the marker is configured to reflect light.

8. The system in accordance with claim 1, wherein the floor area comprises a coating as a registering aid.

9. The system in accordance with claim 1, wherein the second system component is a control unit and is configured to retrieve the scope of treatment from a hospital information system.

10. The system in accordance with claim 1, wherein the third system component is an acoustic signal generator that provides spoken instructions for correcting the spatial distribution.

11. The system in accordance with claim 1, wherein the third system component is configured to indicate the recommended spatial distribution using a specific color or a specific plain text.

12. A method for indicating a recommended spatial distribution of devices configured to be assigned to a patient under medical treatment in a treatment room, the method comprising:
   recording a pre-arranged spatial distribution of the devices using a camera;
   registering the devices in the pre-arranged spatial distribution relative to the patient on a floor area of the treatment room using a control unit;
   checking the pre-arranged spatial distribution relative to a desirable freedom of movement of the devices using the control unit;
   generating a feedback based on the checked spatial distribution using the control unit; and
   indicating the recommended spatial distribution of the devices based on the feedback by a video projector or a acoustic signal generator.

13. The method according to claim 12, further comprising reserving at least one restricted area in the pre-arranged spatial distribution or in the recommended spatial distribution for accommodating at least one further device during an emergency treatment.

14. The method according to claim 12, further comprising assigning a marker to at least one of the devices, the marker configured to emit light pulses, the light pulses representing pulse-coded status information related to the respective device.

15. The method according to claim 12, further comprising retrieving a scope of treatment from a hospital information system, wherein checking the spatial distribution relative to the desirable freedom of movement of the devices is based on the retrieved scope of treatment.

16. The method according to claim 15, wherein the recommended spatial distribution is indicated using a specific color or a specific plain text.

* * * * *